United States Patent [19]

Pitesky

[11] Patent Number: 5,671,753
[45] Date of Patent: Sep. 30, 1997

[54] DISPOSABLE MULTIPLE ALLERGEN TESTING APPARATUS

[76] Inventor: Isadore Pitesky, 4001 Linden Ave., Long Beach, Calif. 90807

[21] Appl. No.: 495,310

[22] Filed: Jun. 27, 1995

[51] Int. Cl.$^6$ ............................................. A61B 10/00
[52] U.S. Cl. ........................................................ 128/743
[58] Field of Search ........................ 128/743; 206/569, 206/570, 363–366

[56] References Cited

U.S. PATENT DOCUMENTS

| | | | |
|---|---|---|---|
| 1,815,568 | 7/1931 | Jacqmein . | |
| 1,869,717 | 8/1932 | Silver . | |
| 2,522,309 | 9/1950 | Simon | 128/743 |
| 2,610,430 | 9/1952 | Neiman . | |
| 2,860,768 | 11/1958 | Smithers . | |
| 2,861,682 | 11/1958 | Hatcher . | |
| 3,289,670 | 12/1966 | Krug et al. | 128/743 |
| 3,435,946 | 4/1969 | Sobek et al. . | |
| 3,502,224 | 3/1970 | Heinze . | |
| 3,556,080 | 1/1971 | Hein . | |
| 4,237,906 | 12/1980 | Havstad et al. | 128/743 |
| 4,265,362 | 5/1981 | Suonvieri | 211/60 R |
| 4,292,979 | 10/1981 | Inglefield, Jr. et al. | 128/743 |
| 4,304,241 | 12/1981 | Brennan | 128/743 |
| 4,607,632 | 8/1986 | Brennan et al. | 128/743 |
| 4,657,138 | 4/1987 | Watson | 206/366 |
| 4,769,941 | 9/1988 | Schmidt | 43/57.1 |
| 4,826,003 | 5/1989 | Levy | 206/443 |
| 4,863,023 | 9/1989 | Payne et al. | 206/346 |
| 4,917,235 | 4/1990 | Feiler | 206/566 |
| 5,154,181 | 10/1992 | Fishman | 128/743 |

*Primary Examiner*—Max Hindenburg
*Attorney, Agent, or Firm*—Fulwider Patton Lee & Utecht, LLP

[57] ABSTRACT

An allergy testing apparatus for applying to a patient a plurality of allergens including a formed tray configured with an upstanding peripheral wall and a horizontal web formed with a plurality of open top recessed wells arranged in predetermined spaced relationships and configured to receive and store a supply of respective allergens therein. A hand held applicator is provided including a horizontal plate integrally formed with a plurality of downwardly projecting applicator picks arranged in complementary spaced relationships with the predetermined spaced relationships of the wells and formed on their respective lower ends with penetration points. The hand held applicator is configured to overlie the tray such that the respective picks may be received within the respective wells to immerse the respective points within the respective allergens.

25 Claims, 1 Drawing Sheet

000
DISPOSABLE MULTIPLE ALLERGEN TESTING APPARATUS

BACKGROUND OF THE INVENTION

1. Field of the Invention

The present invention relates to allergy testing and, more particularly, to a device that allows for simultaneously testing a patient's reaction to a plurality of allergens.

2. Description of the Prior Art

Allergy testing involves subjecting a patient to a wide variety of different allergens to determine which allergens cause allergic reactions in the patient. Such testing requires that the respective allergens be applied beneath the surface of the patient's skin. One conventional method is to individually place a drop of allergen on the patient's skin and then prick the contacted skin so that the allergen will be delivered under the patient's skin. In another method, an allergen is deposited on a pick at the end of an applicator and the patient's skin pricked to deliver the allergen beneath the surface.

In yet another method, portable trays have been employed incorporating upwardly opening wells spaced thereabout for receipt of tubular shaped vial tubes containing respective allergens. The vial tubes are configured for receipt of the picks of the individual applicators to be submersed in the respective allergens for subsequent allergy testing. A device of this type is shown in my U.S. Pat. No. 4,237,906.

Because allergy testing typically involves subjecting the patient to a multitude of allergens, the individual application of such plurality of allergens by individual picks, as set forth in the foregoing methods, is very time consuming, expensive and, in many instances, subjects the patient to prolonged periods of uneasiness and discomfort.

In response to those concerns, others have developed applicators having a multitude of applicator picks so that in one swift application, such multitude of allergens are delivered to the patient simultaneously, minimizing the time required to complete the delivery of allergens while minimizing discomfort to a patient. Forms of such multiple allergen applicators can be found in U.S. Pat. Nos. 4,292,979 and 5,154,181. Although such multiple allergen applicators have been found acceptable for their intended purpose, these applicators have some disadvantageous features associated with them.

For example, the allergy testing apparatus disclosed in U.S. Pat. No. 4,292,979 includes a multitude of applicator picks fixedly attached to a hand held applicator. The applicator picks are arranged for overlying a support base having a plurality of apertures formed therein for removable receipt of disposable vials containing allergens. In operation, the hand held applicator is positioned over the vials to submerse the respective picks in such allergens to wet the picks for subsequent application to the patient. As described, the applicator, support base and picks must be sterilized between uses, a procedure which can be inefficient and time consuming. In addition, the testing apparatus incorporates a plurality of components such that assembly of the applicator, including the individual attachment of the respective picks to the hand held applicator, is time consuming resulting in increased cost of production and increased cost of the testing apparatus as a whole.

In U.S. Pat. No. 5,154,181, a hand held allergy testing apparatus is disclosed having a multitude of applicator needles fixedly attached to a movable applicator member to inject a preset number of allergens under a patient's skin. The testing apparatus requires the use of two hands to administer the multitude of allergens and is thus awkward and cumbersome to use. In addition, the applicator and the entire testing apparatus must be sterilized between uses.

To minimize the time and effort required to sterilize the multiple allergen application devices, others have provided disposable application devices. One such disposable multiple allergen applicator is sold by Lincoln Diagnostics Inc., Decater, Ill. under the trade designation "MULTI-TEST" as shown at 30 USPQ2d 1817 and at 1821 (U.S. TTAB), U.S. Pat. No. 3,556,080. The multiple applicators shown are in the form of plastic frames formed with laterally disposed legs terminating in spaced apart feet defining respective penetration points disposed in a common plane for receipt of respective allergens to be simultaneously applied to a patient. This device suffers the shortcoming that to prepare the applicator for use, the clinician must turn the applicator upside down to access the penetration points and then individually apply the respective allergens to each respective point for subsequent administration of the test to the patient. Such actions are inefficient and increase the time required to administer the allergy test. In addition, the penetration points may be exposed to airborne infectious agents during the process of individually applying the allergens to such points.

Therefore, it is desirable that a disposable multiple allergen application device include a means for pre-wetting the penetration points with the respective allergens in a protected manner to minimize the time and effort required to conduct the allergy test while ensuring sterility of the points.

Hence those skilled in the art have found a need for an improved multiple allergen testing device that allows for simultaneous application of a plurality of allergens under a patient's skin while allowing for convenient disposal of the such testing device after use. In addition, it is desirable that the multiple applicator be constructed for convenient handling in one hand to free the other hand for other uses. Furthermore, there continues to be a need for a testing device which limits the waste materials created by the use thereof. Moreover, the testing device should incorporate a minimum number of components to minimize costs and decrease assembly time. The instant invention addresses such needs.

SUMMARY OF THE INVENTION

Briefly, and in general terms, the present invention is directed to an allergy testing apparatus for applying to a patient a plurality of allergens.

In accordance with the invention, the allergy testing apparatus includes a tray and a hand held multiple allergen applicator. The tray is integrally formed of thermoplastic and is configured with an upstanding peripheral wall and a horizontal web formed with open top recessed wells arranged in predetermined spaced relationships. The wells are configured to receive and store a supply of the respective allergens.

The hand held applicator is integrally formed of thermoplastic and is configured with a horizontal plate formed with a plurality of downwardly projecting applicator picks arranged in complementary predetermined spaced relationships to the spaced relationships of the wells. The respective applicator picks are formed on their respective lower ends with penetration points. The hand held applicator is configured to overlie the tray such that the respective picks may be received within the respective wells to submerse the respective points within the respective allergens.

In a particular aspect of the invention, the wells are formed at their respective top ends with necks of a predetermined configuration and the top ends of the respective picks are formed with downwardly projecting plugs configured to be removably received in stopping relationship in the respective necks.

In a further detailed aspect, the picks are of a predetermined length and terminate in their respective distal tips with a predetermined cross section to be received in close fitting relationship within reduced-in-cross section sinks formed in the bottom of the respective wells.

In another aspect of the invention, spaced apart, upwardly projecting hand grasp handles are formed on the opposite sides of the horizontal plate of the applicator.

Other features and advantages of the invention will become apparent from the following detailed description taken in conjunction with the accompanying drawings, which illustrate by way of example, the features of the invention.

DETAILED DESCRIPTION OF THE PREFERRED EMBODIMENT

Figure 1:
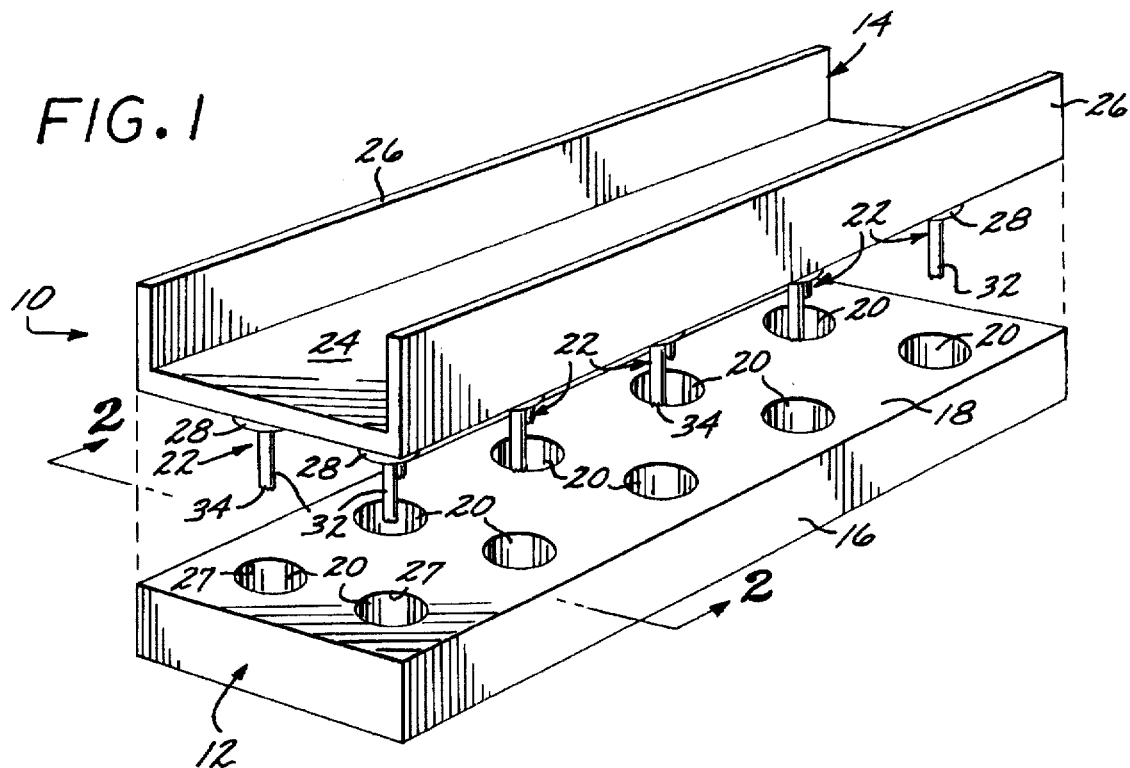
FIG. 1 is a perspective view of a disposable allergy testing apparatus embodying the present invention.

In the following detailed description, like reference numerals will be used to refer to like or corresponding elements in the different figures of the drawings. Referring to the FIGURES, the invention is embodied in a convenient compact, disposable allergy testing apparatus 10 for applying a plurality of allergen testing materials to a patient. The testing apparatus includes a well tray and a hand held allergen applicator that facilitates convenient storage and easy application of such allergens simultaneously.

The hand held applicator includes a plurality of applicator picks to administer the respective plurality allergen under the skin of the patient. The allergy testing apparatus provides for efficient pre-wetting of the applicator picks with respective allergens to save the time that would otherwise be required to apply the respective allergens to each of the plurality of applicator picks immediately before performing an allergy test. In addition, the apparatus provides for efficient use of the allergen testing materials thereby reducing material costs while limiting the amount of residual, unused allergen.

Figure 2:
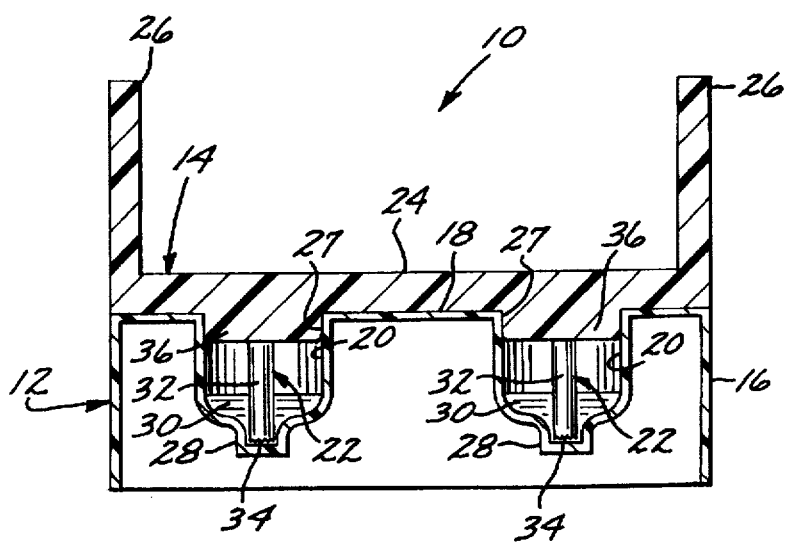
FIG. 2 is a cross sectional view, in enlarged scale, taken along the line 2—2 of FIG. 1.

Referring to FIGS. 1 and 2, the well tray 12 is integrally formed of thermoplastic and is generally in the form of a hollow downwardly opening rectangular box having an upstanding vertical peripheral wall 16, the bottom edge thereof terminating in a horizontal plane to define a bottom support. In the preferred construction, the tray is formed of high strength thermoplastic materials such as PET-G or polycarbonate. The peripheral wall is integrally formed with a horizontal web defining a top wall 18 formed integrally with a plurality of recessed open top allergen wells 20. The wells are formed in predetermined spaced apart relationships into which may be disposed therein a predetermined volume of different respective allergens. The wells, for purposes of illustration, are spaced apart in two adjacent parallel rows and configured to receive in their respective open top ends respective allergen applicator picks, generally indicated at 22, of the hand held applicator 14 described hereinafter.

In general, the hand held applicator 14 includes a horizontal, rectangular flat plate defining a base 24 integrally formed with the plurality of downwardly projecting allergen applicator picks 22 arranged in spaced apart relationships in conformity with the predetermined spaced configuration of the plurality of allergen wells 20. The lateral opposite sides of the hand held applicator is also integrally formed with a pair of longitudinal upwardly projecting handles 26, which may be formed with a slight draft to facilitate removal from a mold during the thermoplastic molding process. The handles are configured to be grasped at their respective top extremities by a clinician. The handles 26 have such a configuration for ease of handling the applicator 14 as well as for ease of applying the requisite compressive force to the skin of the patient to break the surface of such skin.

As shown in FIG. 2, the applicator 14 is configured to cooperate with the well tray 12 such that it may be aligned thereover and positioned in complementary relationship thereon to immerse the respective distal ends of the respective applicator picks 22 within the respective allergens 30 contained in the respective wells providing for convenient storage and packaging. The applicator may be releasably removed from the well tray for application of the respective allergens to the patient.

With particular reference to FIG. 2, the well tray 12 will be described in more detail. In a preferred configuration, the well tray 12 is constructed of lightweight, thin wall, thermoplastic material and may be molded over a forming mold using vacuum forming processes well known by those skilled in the art. As such, the peripheral wall 16 of the well tray 12 may be formed with a slight downwardly diverging draft and the side walls of the respective wells 20 may be formed with a slight converging downwardly draft to facilitate removal of the formed tray from the mold. The wells are generally cylindrical having cylindrical open top ends to define respective necks 27. While the number of wells and mating picks may vary for different applications, I here illustrate two rows of wells and picks with five in each row. The tray is ⅝ inch high, 2½ inches wide, 7 inches long. As shown in FIG. 2, the bottom ends of the respective wells convergingly taper in a smooth curved manner radially inwardly and then downwardly to form respective reduced-in-diameter collection basins defining sinks 28 having respective flat bottom surfaces. The respective wells are formed to have uniform, predetermined depths such that the bottom surface of the collection sinks terminate in a common horizontal plane. The wells serve to hold therein the desired quantities of various liquid allergens 30 which are to be applied to a patient undergoing an allergy test.

With reference to FIG. 2, the hand held applicator 14 will be described in further detail. In the preferred configuration, the applicator 14 may also be constructed of thermoplastic materials and formed, for instance, by an injection molding processes well known by those skilled in the art. Preferably, the hand held applicator is constructed of either polypropylene, acetal, or polycarbonate. Using such a molding process, the applicator picks 22 are formed integrally at their upper extremities with the base 24 of the applicator 14. More particularly, the applicator picks are in the form of elongated stems 32 terminating at their respective bottom extremities in respective penetration points 34 configured to be normally immersed in the respective allergens 30 and formed with sharp jagged edges to pierce the skin surface upon application thereto. The stems 32 of the applicator picks 22 are generally slender and cylindrical, although their particular shape and cross sectional geometry may vary. The respective stems of the applicator picks are further formed with uniform, predetermined lengths such that the penetration points 34 are disposed in a common plane to be simultaneously pressed against the skin of a patient. In addition, the upper ends of the respective applicator picks 22 are formed with respective enlarged-in-diameter concentric, cylindrical well plugs 36 sized for snug receipt within the respective cylindrical necks 27 at the top open ends of the respective wells 20 to stop such wells for retaining the respective allergens 30 stored therein.

It is to be appreciated that the disposable allergy testing apparatus 10 is configured to be conveniently packaged for subsequent sale and distribution to clinicians for performing allergy tests. To assemble and package the allergy testing apparatus, the well tray 12 and hand held applicator 14 may be fabricated as described above and then sterilized using techniques well known to those skilled in the art. Thereafter, predetermined volumes of commonly used pre-selected respective allergens 30 are poured into the respective wells. Thereafter, the applicator may be positioned over the well tray to align the respective applicator picks 22 downwardly over the respective wells 20 and the applicator advanced downwardly thereon to immerse the respective points 38 within the respective allergens 30 as the respective plugs 28 are received within the respective open necks 27 of the wells to stop such wells. The applicator 14 may be advanced downwardly until the horizontal plate 24 of the applicator 14 comes to rest on the top surface of the horizontal web 18. With the horizontal plate and web so engaged, it is to be appreciated that the length of the stems 32 of the respective applicator picks 22 and the depth of the collection sinks 28 at the bottom of the respective wells 20 are so configured to dispose the distal ends of the respective stems and the penetration points 34 thereof in close fitting relationship coaxially within the respective collection sinks while maintaining the respective points 34 in close spaced relationship with, but spaced slightly from, the bottom surface of the respective sinks. This positions the tip such that they will be submersed in the respective allergens in such sinks, even as the volume of such allergens approach depletion while preventing direct engagement with the respective walls of such sinks to thereby maintain the integrity of the sharp jagged edges of such points. It can be appreciated that the fabrication and assembly of the testing apparatus is completed in a minimum number of steps to minimize production costs.

Furthermore, it is to be appreciated that the respective wells may be filled with different selected combinations of allergens 30 for use in performing tests for different allergies. As such, the clinician may select a particular allergy testing apparatus containing a certain combination of allergens to be administered to patients exhibiting particular allergic reactions.

Thereafter, the assembled applicator 14 and well tray 12 may be packaged as by, for instance, vacuum sealing in a protective sterilized plastic cover to package the allergy testing apparatus 10 for storage. In addition, the packaged allergy testing apparatus may be inserted in a box or the like to further protect the testing apparatus from damage or tampering and to facilitate safe shipping and handling. It is to be appreciated that the respective penetration points 34 of the respective applicator picks 22 are thus assembled and packaged for storage to be maintained immersed in the respective allergens 30 of the respective wells 20 ready for use by the medical technician to administer the desired test.

In use, the testing apparatus 10 of the present invention may be stored in the clinician's office for convenient and rapid retrieval ready for immediate use. To perform an allergy testing procedure, the clinician may remove the testing apparatus 10 from the sterile packaging and place the well tray 12 in the palm of one hand and grasp the peripheral wall 16 thereof to support such testing apparatus 10. Then, the clinician can conveniently grasp the applicator 14 with his or her other hand by means of the holders 26 and pull upwardly thereon to release the applicator from the well tray withdrawing the respective distal ends of the respective applicator picks 22 from the respective wells 20. Because the points 34 of the respective picks have been stored in submersed fashion within the respective allergens 30 contained in the wells, as the respective applicator picks are withdrawn therefrom, respective drops of the respective allergens form about the respective points 34. As such, the clinician is relieved of the time consuming and tedious task of applying allergen solutions individually to the respective picks and may apply the picks as a group directly to the patient's skin. This serves to expedite the overall process and contributes significantly to reducing the cost of the treatment. The application of the allergens to the patient is thereby completed in a very short period of time, perhaps in only a matter of seconds.

It is to be appreciated that the applicator 14 may be disposed of after one use, while the tray 12 containing remaining amounts of the respective plurality of allergens 30 in the respective wells 20 may be retained for subsequent allergen applications. As such, a new sterile applicator 14 may be selected and the applicator apparatus stored with such new sterile applicator 14 positioned in covering relationship on the tray 12 with the points 34 of the respective applicator picks 22 thereof submersed in the respective allergens 30.

When the clinician then desires to perform additional allergen testing on this or another patient, he or she may retrieve the testing apparatus 10 to repeat the process with the points 34 of the respective applicator picks 22 having the allergens 30 pre-applied.

As the application of the respective allergens 30 is repeated, the volume of the allergens contained in the respective wells 20 will be gradually depleted. It is to be appreciated that the unique shape of the collection sinks 28 at the bottom of the respective wells 20 provide for an efficient use of the respective allergens. As the respective picks 22 are reintroduced into the wells, the close fitting relationship between the distal ends of the respective picks in the collection sinks 28 will cause the residual allergens to be contained in respective vertical columns in the respective sinks 28 to surround such distal ends such that a sufficient volume of allergen adheres to the respective picks for subsequent application to the patient. As such, the total volume of expensive allergens to be packaged in the wells of the allergy testing apparatus 10 is minimized, reducing costs to the end user while, even as the supply of allergens is being depleted, providing a sufficient volume of the respective allergens pooled in such sinks to be applied to the respective points. As such, the amount of waste allergen material to be disposed of is limited. When the supply of allergens has been depleted, the user may merely discard the relatively inexpensive well tray 12 for disposal with other medical waste material.

From the foregoing, it will be appreciated that the allergy testing apparatus of the present invention provides a convenient device for quick and easy simultaneous application of a plurality of allergens to a particular patient. The testing apparatus may be formed of relatively inexpensive thermoplastic materials allowing for convenient disposal of such testing apparatus after its use. The testing apparatus incorporates few components and is of relatively simple construction providing for cost effective and rapid manufacture.

The apparatus provides for pre-wetted allergen applicator picks to eliminate the step of applying respective allergens to each individual respective applicator pick immediately before performing an allergy test resulting in time savings as well as conservation of expensive allergen testing materials. In addition, the apparatus provides for efficient use of allergen testing materials thereby further reducing costs while limiting the amount of waste allergen material which must be disposed of.

While particular forms of the invention have been illustrated and described, it will also be apparent that various modifications can be made without departing from the spirit and scope of the invention. Accordingly, it is not intended that the invention be limited, except as by the appended claims.

What is claimed is:

1. Disposable allergy testing apparatus for abrading and applying a plurality of allergens to a cutaneous site on a patient and comprising:

a base tray of formed thermoplastic sheet material formed with an upstanding peripheral wall terminating in a bottom support edge and further configured with a horizontal top web formed with a plurality of open top, vertically recessed wells arranged in predetermined spaced relation and configured in their respective bottom extremities with bottom walls and for receipt and storage of respective said plurality of allergens therein; and an applicator device including a horizontal plate formed with a plurality of integrally formed downwardly projecting applicator picks arranged in said predetermined spaced relation and formed on their respective lower ends with respective multiple puncture points for puncturing said patient's skin, said applicator device configured to be positioned on said web for receipt of the respective said picks within the respective said wells to project downwardly and dispose the respective said lower ends in close spaced relationship relative to the respective said bottom walls.

2. The apparatus of claim 1 wherein:

the respective said wells are formed at their respective top ends with necks of a predetermined configuration; and said horizontal plate is formed at the respective top ends of the respective said picks with downwardly projecting plugs configured to be removably received in stopping relationship within the respective said necks.

3. The apparatus of claim 1 wherein:

the respective said picks are of a predetermined length and are configured at their respective distal tips with a predetermined cross section; and the respective said wells at their bottom ends convergingly taper downwardly and inwardly to form the respective said sinks with a cross section to, when said plate is positioned on said web, receive in close fit relationship the respective said tips.

4. The apparatus of claim 1 wherein:

said applicator is formed with a pair of integral hand grasp handles upwardly projecting from the opposite sides of said plate.

5. The apparatus of claim 1 wherein:

said tray is formed with said peripheral wall integral with said web projecting around the entire periphery of said web.

6. The apparatus of claim 1 wherein:

said applicator is constructed of thermoplastic.

7. The apparatus of claim 1 wherein:

said tray is formed with said web, wall and wells integral with one another.

8. The apparatus of claim 1 wherein:

said tray is configured with said web arranged in a pair of rows numbering substantially five in each row.

9. The apparatus of claim 1 wherein:

said tray is configured with said peripheral wall about ⅝ inch high.

10. The apparatus of claim 1 wherein:

said base tray is constructed of polycarbonate.

11. The apparatus of claim 1 wherein:

said base tray is constructed with a thin sheet defining said top web to be disposed in a horizontal plane, said sheet being formed with integral, downwardly projecting, thin walled cups depending below said horizontal plane to define the respective said wells.

12. The apparatus of claim 1 wherein:

said peripheral wall is formed with a draft to taper downwardly and outwardly to facilitate removal from a forming mold.

13. The apparatus of claim 1 wherein:

said wells are formed with cylindrical cup shaped thin walls which wails taper downwardly and radially inwardly from said top wall to form a draft to facilitate removing from a forming mold.

14. The apparatus of claim 13 wherein:

said peripheral wall is formed with a draft to angle downwardly and outwardly to facilitate removal from a forming mold.

15. The apparatus of claim 1 wherein:

said wells are cup shaped and are formed with cylindrical side walls configured to curve radially inwardly and then project downwardly to form respective cylindrical reduced-in-diameter sinks for coaxial receipt of said lower ends of said picks.

16. The apparatus of claim 1 wherein:

said picks are constructed of plastic and are solid in cross section.

17. The apparatus of claim 1 wherein:

said applicator is elongated and is formed with at least one longitudinally upstanding flange defining said handle.

18. Disposable allergy testing apparatus for applying a plurality of allergens to a patient and comprising:

a base tray of formed thermoplastic sheet material formed with an upstanding peripheral wall terminating in a bottom support edge and further configured with a horizontal top web formed with a plurality of vertically recessed wells arranged in predetermined spaced relation having open top ends defining necks of a predetermined configuration, said wells configured in their respective bottom extremities with sinks for receipt and storage of a predetermined volume of the respective said plurality of allergens therein; and an applicator device including a horizontal plate formed with a plurality of integrally formed downwardly projecting applicator picks arranged in said predetermined spaced relation formed on their respective top ends with respective downwardly projecting plugs configured to be removably received in stopping relationship in the respective said necks and formed on their respective lower ends with respective abrading points, said applicator device configured to be positioned on said web for receipt of the respective said picks within the respective said wells to project downwardly and to immerse the respective said ends within the respective said sinks and for receipt of the respective said plugs in stopping relationship within the respective said necks.

19. The apparatus of claim 18 wherein:

the respective said picks are of a predetermined length and are configured at their respective distal tips with a predetermined cross section; and the respective said wells at their bottom ends convergingly taper downwardly and inwardly to form the respective said basins with a cross section to, when said plate is positioned on said web, receive in close fit relationship the respective said tips.

20. The apparatus of claim 18 wherein:

said applicator is formed with a pair of integral hand grasp handles upwardly projecting from the opposite sides of said plate.

21. The apparatus of claim 18 wherein:

said tray is formed with said peripheral wall integral with said web projecting around the entire periphery of said web.

22. The apparatus of claim 18 wherein:

said applicator is constructed of thermoplastic.

23. The apparatus of claim 18 wherein:

said tray is formed with said web, wall and wells integral with one another.

24. The apparatus of claim 18 wherein:

said tray is configured with said web arranged in a pair of rows numbering substantially five in each row.

25. The apparatus of claim 18 wherein:

said tray is configured with said peripheral wall about $5/8$ inch high.

* * * * *